United States Patent [19]

Lin

[11] Patent Number: 4,720,573

[45] Date of Patent: Jan. 19, 1988

[54] PROCESS FOR SYNTHESIS OF GLUTAMIC ACID FROM ACRYLATE, AMIDE AND SYNTHESIS GAS

[75] Inventor: Jiang-Jen Lin, Round Rock, Tex.

[73] Assignee: Texaco Inc., White Plains, N.Y.

[21] Appl. No.: 891,094

[22] Filed: Jul. 31, 1986

[51] Int. Cl.$^4$ ............................................. C07C 103/66
[52] U.S. Cl. .................................... 560/171; 560/169; 562/573
[58] Field of Search .................... 560/169, 155, 171; 562/573

[56] References Cited

U.S. PATENT DOCUMENTS 3,766,266 10/1973 Wakamatsu .......................... 562/578
4,264,515 4/1981 Stern .................................. 562/450

OTHER PUBLICATIONS

Murata, Bull. Chem. Soc. Jpn., 53, pp. 214–218, (1980).

*Primary Examiner*—Michael L. Shippen
*Attorney, Agent, or Firm*—Jack H. Park; Kenneth R. Priem; Cynthia L. Kendrick

[57] ABSTRACT

A process for the synthesis of glutamic acid intermediate from an acrylate, amide and syngas by reacting them in the presence of a catalyst comprising a cobalt-containing compound, a bis-phosphine ligand and a solvent at a pressure of at least 500 psi and a temperature of at least 50° C. and thereafter extracting the glutamic acid.

13 Claims, No Drawings

PROCESS FOR SYNTHESIS OF GLUTAMIC ACID FROM ACRYLATE, AMIDE AND SYNTHESIS GAS

FIELD OF THE INVENTION

This invention relates to the synthesis of glutamic acid from methyl or ethyl acrylates, an amide and syngas.

More particularly this invention uses a cobalt catalyst and a bis-phosphine ligand to synthesize N-acetyl-glutamic acid in one step from methyl or ethyl acrylate and an amide and synthesis gas with high yield and linearity using mild pressures and temperatures.

BACKGROUND OF THE INVENTION

Early attempts to synthesize α-amino acids or derivatives thereof by reacting a Schiff base or a nitrile with carbon monoxide and hydrogen were unsuccessful. [Bull. Chem. Soc. Japan 33 (160) 78]

U.S. Pat. No. 3,766,266 to Wakamatsu discloses a method of producing an N-acyl-α-amino acid which comprises holding an aldehyde, an amide of a carboxylic acid and carbon monoxide at a temperature of 10° to 300° C. and a pressure of at least 500 atm. in the presence of a carbonylation catalyst until said N-acyl-α-amino acid is formed.

In *Chem. Comm.* 1540 (1971), Wakamatsu, et al. disclose a cobalt-catalyzed reaction which gives various N-acyl amino-acids from an aldehyde, an amide and carbon monoxide. In this disclosure, while benzaldehyde was used as the starting aldehyde, there was no corresponding β-phenyl-substituted amino acid obtained. Instead of the expected amino acid product, a imine was obtained by a simple "amination" reaction.

An article by Parnaud, et al., in *Journal of Molecular Catalysis*, 6 (1979) 341-350, discusses the synthesis potential and the catalytic mechanism for the reaction wherein N-acyl-α-amino acids are produced by reacting an aldehyde, CO and an amide in the presence of dicobalt octacarbonyl.

In amidocarbonylation, the aldehyde can be generated in situ from allyl alcohol, alkyl halides, oxiranes, alcohols and olefins followed by the reaction with an amide and carbon monoxide to produce an N-acyl-α-amino acid.

A related Patent, U.S. Pat. No. 3,996,288 discloses that when an alcohol or certain of its ester derivatives is held at 50° C. to 200° C. and 10 to 500 atm. in the presence of hydrogen, carbon monoxide, the amide of a carboxylic acid and a carbonylation catalyst, an aldehyde having one more carbon atom than the alcohol or ester is formed in good yield. If the amide has at least one active hydrogen atom on its amide nitrogen, it further reacts with the aldehyde and carbon monoxide to form an N-acyl-amino acid.

Hirai, et al. discuss a process for combining the transition metal catalyzed isomerization of allyl alcohol to aldehyde and cobalt catalyzed amidocarbonylation to provide a route from allylic alcohols to N-acyl-α-amino acids. See

*Tetrahedron Letters*, Vol. 23, No. 24, pp. 2491-2494, 1982.

U.S. Pat. No. 4,264,515 by R. Stern et al. discloses a process for obtaining terminal N-acyl-α-amino acids by a reaction catalyzed by a cobalt carbonylation catalyst wherein the aldehyde is produced in situ from olefins and CO/H$_2$ mixtures. An unsaturated vegetable oil or C$_8$-C$_{30}$ monoolefinic compound is reacted with an amide, carbon monoxide and hydrogen in the presence of a cobalt catalyst. The process is operated in one step and provides for increased selectivity.

A recent review article, published by Ojima in Journal of Organometallic Chemistry, 279 (1985), 203-214, discussed the synthesis of N-acetyl-α-amino acids from (a) the isomerization-amidocarbonylation of allylic alcohols, (b) the isomerization-amidocarbonylation of oxiranes and (c) the hydroformylation-amidocarbonylation of trifluoropropene. The hydroformylation-amidocarbonylation of trifluoropropene in Ojima's work demonstrated a surprising regioselectivity for products 1 and 2.

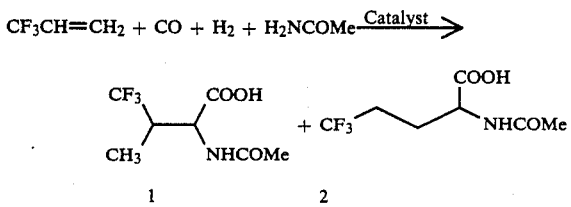

The results demonstrated in that work showed the highly regioselective synthesis of N-acetyltrifluorovaline (1) (94%) and N-acetyltrifluoronorvaline (2) (96%) in high yields by using Co$_2$(CO)$_8$—Rh$_6$(CO)$_{16}$ and Co$_2$(CO)$_8$ as catalysts respectively. The results showed the surprising difference in yield when using Co$_2$(CO)$_8$ as opposed to Co$_2$(CO)$_8$—Rh$_6$(CO)$_{16}$ catalysts in the special case of the fluoroolefin substrate.

The use of amidocarbonylates reactions in substrates containing a functionality such as ester group (that is, methyl or ethyl acrylate) in one step to produce the corresponding monoester of the N-acetylglutamate has not been previously disclosed. In a British patent specification No. 828,946 (1960) titled "Synthetic Process for Producing Glutamic Acid From Acrylonitrile", the reaction involved the hydroformylation of acrylonitrile followed by hydrocyanic acid and ammonia reaction in two steps. In a related patent, U.S. Pat. No. 3,766,266, a two-step synthesis from acrylate to aldehyde is disclosed, followed by the reaction of acetamide and carbon monoxide to produce the corresponding final product, glutamic acid. The reaction conditions in the two separate steps are slightly different.

The present invention involves the use of Bis-1,3-(diphenylphosphino)propane in combination with dicobalt octacarbonyl to achieve the conversion of acrylate into glutaric acid derivatives in a single step. K. Murata et al reported earlier the effect of Di(tertiary phosphine) ligand in hydroformylation of methyl acrylate. (Bull. Chem. Soc. Jpn., 53, 214–218 (1980). The reaction rate was related to the species of bidental phosphine ligand and Co-P ratio. J. Molecular Catalysis 23 (1984), 121–132 and Chem. Commu. (1979) 785, have reported the similar results in CO/H$_2$O reactions. However, J. Organometallic Chem. 1985, 283, No. 1–3, reported that HCo(CO)$_2$(Bu$_2$PCH$_2$CH$_2$PBu$_2$) was found to be an inactive catalyst for olefin hydroformylation and required an activation period.

The results of the instant invention using Co$_2$(CO)$_8$ with a bis-phosphine ligand in a one step synthesis are novel in the following respects:

(1) The presence of 1,3-bis-diphenylphosphino propane stabilizes dicobalt octacarbonyl and allows the reaction to proceed predictably at a low temperature in comparison with dicobalt octacarbonyl alone.

(2) The combined Co$_2$(CO)$_8$ and bis-phosphine ligand catalyst performs the reaction under milder reaction conditions, for example, as low as 800 psi.

(3) Rhodium species used in the comparative example affects regioselectivity.

Previous methods known in the art for preparing glutamic acid involve two steps. It would be an advance in the art to devise an inexpensive, one-step method of making glutamic acid in high yields with a great degree of linearity under mild conditions from an acrylate, an amide and syngas.

The instant invention relies on a cobalt catalyst system for the synthesis of glutamic acid from methyl or ethyl acrylate, acetamide and syngas wherein yields of glutamic acid are as high as 80% and a linearity of ~80% is observed using very mild reaction conditions. After the ester intermediate is obtained, extraction by a acid/base medium such as Na$_2$CO$_3$ or H$_3$PO$_4$ are used to obtain the glutamic acid in good yield.

SUMMARY OF THE INVENTION

This invention concerns a one-step process for synthesizing glutamic acid intermediates which comprises contacting a mixture of acrylates, amides and syngas (carbon monoxide and hydrogen) with a catalyst comprising a cobalt-containing compound and a bis-phosphine ligand in the presence of a solvent at a pressure of at least 500 psi and a temperature of at least 50° C. or 150° C.

Acrylates are used to produce the N-acetylglutamate intermediates in up to 80% yield with up to 80% linearity.

It was found, by reference by Comparative Example VIII, using rhodium, that regioselective hydroformylation of acrylate at the beta position is the key to glutamic acid synthesis.

DETAILED DESCRIPTION OF THE INVENTION

In the narrower and more preferred practice of this invention N-acetylglutamate intermediates are prepared from a mixture of acrylates, amides, carbon monoxide and hydrogen by a process which comprises contacting said mixture with a catalyst system comprising a cobalt-containing compound and a bis-phosphine ligand in a substantially inert solvent at a temperature of at least 50° C. and a pressure of at least 500 psi until substantial formation of the desired glutamic acid intermediate has been achieved.

The glutamic acid intermediates are in liquid form at room temperature. These intermediates are predominantly linear. After extraction with organic solvent from a mineral acid or base such as Na$_2$CO$_3$ or H$_3$PO$_4$, the product glutamic acid is obtained in good yield. The market for glutamic acid is one of the largest in the amino acid group.

The reaction for producing linear glutamate intermediates from acrylates can be represented by the following equation:

Equation I

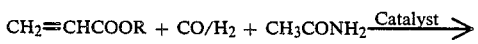

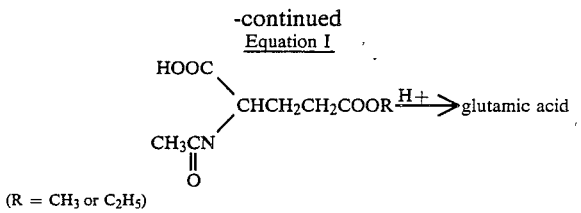

(R = CH$_3$ or C$_2$H$_5$)

The reaction for producing an N-acetylglutamate intermedate from ethyl acrylate can be represented by the following equation:

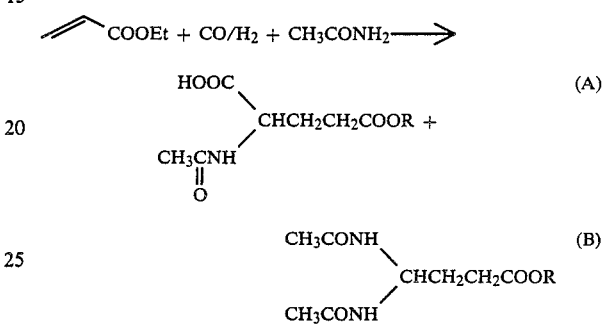

In general, two products-N-acetyl-glutamate (A) and 4,4-bis(acetylamido)butyrate (B) were isolated. Compound (B) is hydrolyzed and carbonylated into compound (A) under higher syngas pressure or temperature. Both compounds led to the desired glutamic acid through the selective hydroformylation of product (C) at the β position of acrylate.

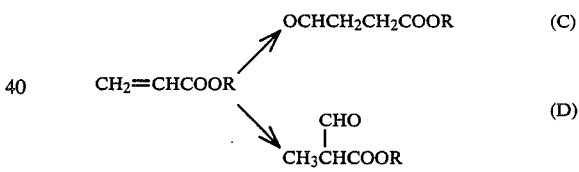

In Comparative Example VIII, a rhodium catalyst was used and compound (D) was obtained with undesired side products.

Recovery of the glutamic acids from the reaction product can be carried out by extraction. Two steps of extraction may be used: (1) acetate solvent extractions from the Na$_2$CO$_3$/H$_2$O layer to remove impurity and (2) acetate solvent extraction from the H+/H$_2$O layer to obtain the pure products. In the embodiment of this invention the product was identified by NMR and IR.

The catalyst system suitable for the practice of this invention comprises a cobalt-containing compound and a bis-phosphine ligand in a substantially inert solvent. The bis-phosphine ligand is found to be essential to stabilize the cobalt-containing compound during amidocarbonylation. The controlled experiments represented by comparative Example VIII show the presence of Rh can cause hydroformylation at the alpha position of the methyl acrylate, followed by a side reaction such as Michael addition and lead to a different reaction path. Regioselective hydroformylation of acrylate at the beta position is the key to glutamic acid synthesis. Furthermore, the instant catalyst system provides important advantages over the use of cobalt alone:

(1) It gives higher yields and selectivities of the N-acetylglutamate intermediate acid products in one-step under milder conditions.

(2) It was possible to obtain as high as 80% linear glutamic acid product.

In the process of this invention it is preferable that the cobalt-containing compound be used with a bis-phosphine ligand. Ligands which work well in this respect include those of the formula $$Ph_2P(CH_2)_xPPh_2$$

wherein $x = 1$ to 6.

The preferred compounds are 1,3-bis(diphenylphosphino)propane and 1,2-bis(diphenylphosphino)ethane.

It is worthwhile to note that rhodium species seem to have an adverse effect on production of glutamic acid as shown in our comparative Example VIII. It was found the rhodium catalyst performed the hydroformylation at the alpha position of the methyl acrylate, followed by a side reaction such as Michael addition and led to a different reaction path. Therefore, a combination of Rh-Co bicatalyst would not be suitable for this process.

The cobalt-containing compound may take many different forms. For instance, the cobalt may be added to the reaction mixture in the form of a variety of inorganic or organic cobalt salts, or cobalt carbonyls. The cobalt may, for example, be added as a cobalt halide such as cobalt bromide or cobalt chloride, or it may be added as the salt of an aliphatic or aromatic carboxylic acid such as, for example, cobalt formate, cobalt acetate, cobalt butyrate, cobalt naphthenate, and cobalt stearate. The cobalt carbonyl may be tetracobalt dodecacarbonyl or dicobalt octacarbonyl. The preferred cobalt-containing compound is dicobalt octacarbonyl.

The physical parameters which are desirable for the feedstock of this invention for producing N-acetylamino acid can be described as follows:

The starting acrylate substrates are represented by the structure $$CH_2=CHCOOR.$$

The R-group can be methyl or ethyl. Particularly good results are obtained using ethyl acrylate.

Suitable amide-containing coreactants that are useful in the amidocarbonylation reaction have the general structure:

$$\underset{\underset{R_1CNHR_2}{\|}}{O}$$

where the $R_1$ group may be a combination of aryl, alkyl, arylalkyl and alkylaryl hydrocarbonyl radicals, or hydrogen, including the methyl, ethyl, butyl, n-octyl, phenyl, benzyl and chlorophenyl groupings. The $R_2$ group must be hydrogen in order to obtain glutaric acid derivatives. Examples of suitable amide coreactants include acetamide, benzamide, formamide, and lauramide. The preferred coreactant is acetamide.

The carbon monoxide employed need not satisfy particular purity requirements although catalyst contaminants should be avoided if the reaction is intended to continue over an extended period. Particularly in continuous operations, but also in batch experiments, the carbon monoxide and hydrogen as may also be used in conjunction with up to 10% by volume of one or more other gases. These other gases may include one or more inert gases such as argon, nitrogen and the like or they may include gases that may, or may not, undergo reaction under carbon monoxide hydrogenation conditions, such as carbon dioxide, hydrocarbons, such as methane, ethane, propane and the like, ethers, such as dimethyl ether, methyl ethyl ether and diethyl ether, alkanols, such as methanol, and the like.

As characterized above, this process is operated as a homogeneous liquid phase mixture. The reaction is preferably carried out in an inert solvent. Preferred inert solvents are those which permit at least partial dissolution of the cobalt and bis-phosphine ligand catalyst precursors, the amide and the olefin. These are generally polar solvents of the ester, ether, ketone, amide, sulfoxide or aromatic hydrocarbon type, for example.

Methyl and ethyl acetate are examples of suitable solvents. Other polar solvents are ethers, such as p-dioxane, methyl tertiary butyl ether, methyl tertiary amyl ether or tetrahydrofuran, tertiary amides, such as dimethyl formamide, dimethyl sulfoxide and ethylene carbonate.

The preferred solvent is ethyl acetate.

In all these synthesis in order to achieve a high degree of selectivity the amount of carbon monoxide, acrylate and amide present in the reaction mixture should be sufficient to at least satisfy the stoichiometry of the desired formation of glutamic acid intermediates as shown in Equation I above. Excess carbon monoxide over the stoichiometric amount may be present and is desirable.

The quantity of cobalt-containing compound and bis-phosphine ligand to be used in the catalyst of the invention may vary. The process is conducted in the presence of a catalytically effective quantity of the active cobalt-containing compound which gives the desired product in reasonable yield. The reaction proceeds when employing as little as about 0.1 weight percent of the cobalt-containing compound based on the total weight of the reaction mixture. The upper concentration is dictated by a variety of factors including catalyst cost, partial pressures of carbon monoxide and hydrogen, operating temperature, etc. A cobalt-containing concentration of from about 0.1 to about 10 percent, along with a bis-phosphine ligand concentration of from about 0.1 to 1.0 molar ratio based on phosphine to cobalt is generally desirable in the practice of this invention.

Particularly superior results are obtained when the above-noted components of the catalyst system are combined as follows on a molar basis: Cobalt-containing compound, to bis-phosphine ligand 10:1 to 1:1 in molar ratio.

The operating conditions may vary over a wide range. The reaction temperature may vary from 25° C. to 300° C. The preferred temperature is from 120° C. to 150° C. The pressure may range from 500 psi to 3000 psi or more. It appears that higher selectivities are obtained when operating at moderate pressures, in the range from 800 to 2000 psi.

The amidocarbonylation reaction of this invention is best conducted in a carbon monoxide-rich atmosphere, although some hydrogen gas should also be present in order to achieve maximum cobalt catalyst activity. The hydrogen to carbon monoxide molar ratio in the reactor may be varied, for example, within the range from 20:1 to 1:20, but preferably it should be rich in carbon monoxide and the $H_2$:Co ratio should be in the range 5:1 to 1:5.

The desired products of the synthesis using acrylate olefins are glutamic acid intermediates, such as, for example N-acetylglutamate. Also formed are significant amounts of methyl 4,4-bis(acetamido)butyrate by-products. Each of these products, including by-products can be recovered from the reaction mixture by conventional means such as extraction.

The novel process of the invention can be conducted in a batch, semi-continuous or continuous manner. The catalyst can be initially introduced into the reaction zone batchwise, or it may be continuously or intermittently introduced into such a zone during the course of the synthesis reaction. Operating conditions can be adjusted to optimize the formation of the desired glutamic acid product, and said material may be recovered by methods known to the art, such as extraction. A fraction rich in the catalyst components may then be recycled to the reaction zone, if desired, and additional products generated.

The products have been identified in this work by one or more of the following analytical procedures: viz, gas-liquid phase chromatography (glc), gas chromatography/infrared spectroscopy (GC/IR), nuclear magnetic resonance (nmr) and elemental analysis, or a combination of these techniques. Analysis have for the most part, been by molar weight; all temperatures are in degrees centigrade and all pressures in pounds per square inch (psi).

The yield (mole %) of N-acetylglutamate derivative in this synthesis using an acrylate is estimated basis Equation I using the formula:

$$\frac{\text{Moles of N—acetylglutamate acids obtained}}{\text{Moles of acrylate charged}} \times 100\%$$

To illustrate the process of the invention, the following examples are given. Examples I-IX demonstrate the method of using acrylates in the process of this invention. It is to be understood, however, that the examples are given in the way of illustration and are not to be regarded as limiting the invention in any way.

EXAMPLE 1

A 300 ml stainless-steel stirred autoclave was charged dicobalt octacarbonyl (1.02 g, 3.0 mmoles), bis-1,3-(diphenylphosphino)propane (0.312 g, 0.76 mmoles), methyl acrylate (17.2 g, 200 mmoles), acetamide (11.8 g, 200 mmoles) and ethyl acetate (20 g). The reactor was purged of air with the mixture of $CO/H_2$ (1:1 ratio) and heated to 130° C. At the temperature range of 123°–140° C., the pressure was increased to 800 psi and held for four hours. During the process, the increment of syngas was added and totally 490 psi of syngas consumption was recorded. The reactor was cooled to room temperature, excess gas vented and the liquid products (52.1 g) was recovered.

The H-nmr analysis showed to major products at 1.25 to 1.0 molar ratio of Compounds I and II:

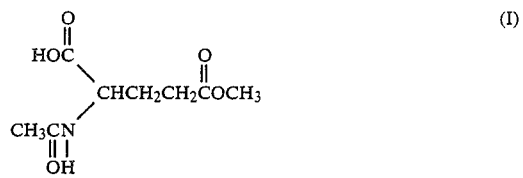

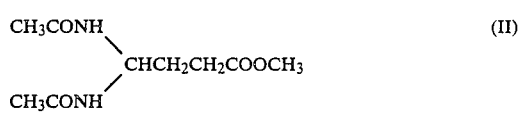

EXAMPLE II

A glass-lined rocking autoclave was charged with dicobalt octacarbonyl (0.34 g, 1 mmole), bis-1,3-(diphenylphosphino)propane (0.416 g, 1 mmole), methyl acrylate (8.6 g, 100 mmoles), acetamide (5.9 g 100 mmoles) and ethyl acetate (10 g). The reactor was purged with syngas, pressured at 800 psi ($CO/H_2 = 1:1$) and heated to 130° C. At this temperature, the pressure was increased to 2000 psi and held for 4 hours. The recovered liquid product solution (27.7 g) was analyzed by H-nmr and showed ca. 70% yield to product I and II at 3.5 to 1.0 ratio.

EXAMPLE III

The identical experimental procedures of Example I were employed. The reactor was charged with dicobalt octacarbonyl (0.34 g, 1 mmole), 1,3-bis(diphenylphosphino)propane (0.206 g, 0.5 mmole), ethyl acrylate (10.0 g, 100 mmoles), acetamide (5.9 g, 100 mmoles) and toluene (20 g).

The reaction conditions were ca. 130° C., 800 psi ($CO/H_2 = 1:1$), and 4 hours. The recovery product solution contained two layers: 20.9 g for the top layer and 15.4 g for the bottom layer. The bottom layer solution contained product III and IV at 3.7 to 2.0 molar ratio.

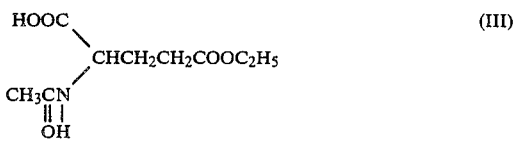

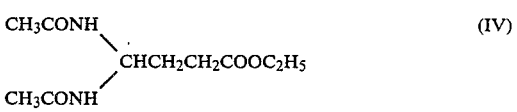

EXAMPLE IV

Procedures identical to those of Example I were employed. The reactor was charged with dicobalt octacarbonyl (0.34 g, 1 mmole), bis-1,3-(diphenylphosphino)propane (0.206 g, 0.5 mmole), methyl acrylate (8.6 g, 100 mmoles), acetamide (5.9 g, 100 mmoles) and ethyl acetate (25.0 g). The reaction conditions were 800 psi ($CO/H_2 = 1:1$), ca. 130° C. and 4 hours.

The product solution (40.6 g) showed the molar ratio of I:II at 2.4:1.0.

EXAMPLE V

The experimental procedures of Example I were repeated. The reactor was charged with dicobalt octacarbonyl (0.34 g, 1 mmole), bis-(1,3-diphenylphosphino)propane (0.206 g, 0.5 mmole), methyl acrylate (8.6 g, 100 mmoles), acetamide (5.9 g, 100 mmoles) and toluene (25 g). The reaction conditions were 114°–139° C., 800 psi and 4 hours. The product solution contained two layers. The top layer solution 26.6 g and the bottom layer solution 13.0 g. The H-nmr analysis of the bottom layer showed the presence of product I:II at 2.7:1.0 molar ratio.

EXAMPLE VI (Comparative)

The experimental procedures of Example I were repeated. The reactor was charged with dicobalt octacarbonyl (0.17 g, 0.5 mmoles), bis-1,3-(diphenylphosphino)propane (0.103 g 0.25 mm), methyl acrylate (8.6 g, 100 mmoles), acetamide (5.9 g, 100 mmoles) and toluene (25 g). The reaction conditions were 116°–124° C., 800 psi and 4.5 hours. The product solution contained the recovery starting material only.

The ratio of catalyst to substrate and the reaction temperature are important factors for amido acid synthesis.

EXAMPLE VII (Comparative)

Procedures identical to those of EXAMPLE VI were used, except no acetamide was used. The reactor was charged with Co$_2$(CO)$_8$ (0.17 g, 0.5 mmole), bis-1,3-(diphenylphosphino)propane (0.103 g, 0.25 mmole), methyl acrylate (8.6 g, 100 mmoles) and toluene (25.0 g). The reaction conditions were ca. 120° C., 800 psi and 3.0 hours. The analysis of the product solution showed 93% conversion of methyl acrylate and 91% selectivity to methyl ester of 3-formyl propionic acid (V).

OHCCH$_2$CH$_2$COOCH$_3$         (V)

The above two comparative examples indicated two-step reactions involved in process (a) hydroformylation of acrylate to 3-formyl propionate and process (b) amidocarbonylation of (V) to amidoacid, required different conditions

EXAMPLE VIII

Experimental procedures similar to EXAMPLE VI were employed, except HRh(CO)(PPh$_3$)$_3$ was used instead of dicobalt octacarbonyl. Under the similar reaction conditions there was no amido acid product observed. It was found that Rh catalyst performed the hydroformylation at the alpha position of the methyl acrylate, followed by a side reaction such as a Michael addition led to a different reaction path.

EXAMPLE IX

A glass-lined reactor was charged with dicobalt octacarbonyl (5.1 g, 15 mmoles), acetamide (53 g, 898 mmoles), ethyl acrylate (75 g, 750 mmoles), and p-dioxane (150 g). The reactor was purged of air and pressured with CO/H$_2$ (1:1 ratio) to 500 psi. The system was heated to 130° C.–153° C., then pressured with CO/H$_2$ to 2000 psi. During two hours reaction time, 2000 psi of pressure was maintained by frequently adding increments of CO/H$_2$ gas. After cooling to room temperature, a homogeneous, light-brown solution (314.3 g) was recovered. An aliquot of the product mixture was added with 10% Na$_2$CO$_3$ and then solid K$_2$CO$_3$ to aliquot the PH=10. The solution was extracted twice by methyl acetate to remove the by-products. The aqueous solution was then adjusted with 85% phosphoric acid until PH2 and again extracted with ether and methyl acetate to afford 126 g of compound (I). The structure (I) was confirmed by H-NMR and IR.

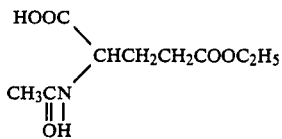

The cobalt contamination in the product was 118 ppm after one extraction and was 7.0 ppm after the second extraction.

What is claimed is:

1. A process for the synthesis of a glutamic acid intermediate represented by the structure

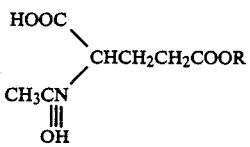

wherein R = methyl or ethyl, from the reaction of an acrylate, amide and syngas in the presence of a catalyst comprising a cobalt-containing compound, a bis-phosphine ligand and a solvent at a pressure of 500 to 5,000 psi and a temperature of 50° to 160° C. and thereafter extracting the glutamic acid precursor.

2. The process of claim 1 wherein the cobalt-containing compound is selected from the group consisting of cobalt carbonyls, cobalt halides and cobalt carboxylates.

3. The process of claim 1 wherein the cobalt-containing compound is selected from the group consisting of dicobalt octacarbonyl, cobalt(II) acetate, cobalt(II) chloride and cobalt(II) bromide.

4. The process of claim 3 wherein the cobalt-contaning compound is dicobalt octacarbonyl.

5. The process of claim 1 wherein the bis-phosphine ligand is selected from the group consisting of 1,3-bis(-diphenylphosphino)propane, 1,6-bis(diphenylphosphino)hexane and 1,2-bis(diphenylphosphino)ethane.

6. The process of claim 5 wherein the bis-phosphine ligand is of the formula

Ph$_2$P(CH$_2$)$_x$PPh$_2$, where X=1–6.

7. The process of claim 5 wherein the bis-phosphine ligand is 1,3-bis-(diphenylphosphino)propane.

8. The process of claim 1 wherein the solvent is a acetate, ether or aromatic compounds.

9. The process of claim 1 wherein the solvent is selected from the group consisting of methyl acetate, ethyl acetate, toluene, xylene and p-dioxane.

10. The process of claim 1 wherein the pressure range is 800 psi to 3000 psi.

11. The process of claim 1 wherein the temperature range is 100° C. to 180° C.

12. The process of claim 1 wherein the temperature range is 120°–150° C.

13. The process of claim 1 wherein the glutamic acid precursor is 4,4-bis(acetylamido)butyric acid ester represented by the structure:

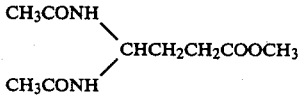

* * * * *